United States Patent [19]

Diehl et al.

[11] Patent Number: 5,210,214
[45] Date of Patent: May 11, 1993

[54] PREPARATION OF INDOLENINES

[75] Inventors: Klaus Diehl, Hassloch; Martin Fischer, Ludwigshafen; Manfred Dimmler, Darmstadt-Schauernheim, all of Fed. Rep. of Germany

[73] Assignee: BASF Aktiengesellschaft, Ludwigshafen, Fed. Rep. of Germany

[21] Appl. No.: 866,586

[22] Filed: Apr. 10, 1992

[30] Foreign Application Priority Data

Apr. 19, 1991 [DE] Fed. Rep. of Germany ....... 4112841

[51] Int. Cl.[5] .................. C07D 209/08; C07D 209/86; C07D 209/88
[52] U.S. Cl. .................... 548/439; 548/448; 548/449; 548/450; 548/451; 548/469; 548/503; 548/509; 548/510; 548/511
[58] Field of Search ............. 548/439, 450, 451, 504, 548/507, 509, 510, 511, 469, 448, 449, 503

[56] References Cited

U.S. PATENT DOCUMENTS 4,062,865 12/1977 Moggi .............................. 260/319.1
4,225,333 3/1981 Opgenorth et al. .............. 260/319.1

FOREIGN PATENT DOCUMENTS 8097 2/1980 European Pat. Off. ............ 548/439

*Primary Examiner*—Patricia L. Morris
*Attorney, Agent, or Firm*—Herbert B. Keil

[57] ABSTRACT

A process for preparing indolenines of the formula I

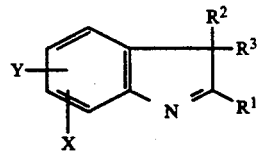

where
R[1], R[2] and R[3] are independently of one another hydrogen, $C_1$–$C_{20}$-alkyl, $C_2$–$C_{20}$-alkenyl, $C_3$–$C_8$-cycloalkyl, aryl, $C_7$–$C_{20}$-alkylphenyl, $C_7$–$C_{20}$-phenalkyl, or R[1] and R[2] or R[1] and R[3] together are an unsubstituted or $C_1$–$C_{12}$-alkyl-substituted $C_3$–$C_8$-alkylene chain,
X and Y are independently of one another hydrogen, $C_1$–$C_8$-alkyl, $C_1$–$C_8$-alkoxy, $C_2$–$C_8$-alkoxyalkyl, $C_2$–$C_8$-alkoxycarbonyl, $C_1$–$C_4$-alkylsulfonyl, halogen, nitro or cyano, by reacting a 4-methylene-1,3-dioxolan-2-one of the formula II

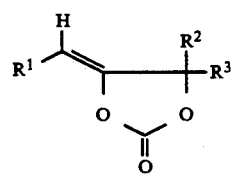

where R[1], R[2] and R[3] are each as defined above, with an aniline of the formula III

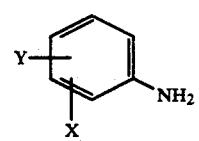

where X and Y are each as defined above, in the presence of a Lewis acid and in the presence or absence of a halide of main group 1 or 2 of the Periodic Table at from 100° to 350° C. and at from 1 to 50 bar, comprises carrying out the reaction in a polar solvent.

9 Claims, No Drawings

PREPARATION OF INDOLENINES

The present invention relates to an improved process for preparing indolenines from 4-methylene-1,3-dioxolan-2-ones and anilines at elevated temperatures in the presence of a mixture of a Lewis acid and a halide of main group 1 or 2 of the Periodic Table by carrying out the reaction in a polar solvent.

EP-A-8097 discloses that indolenines are obtainable in a two-stage heterogeneous reaction from 4-methylene-1,3-dioxolan-2-ones via 4-methylene-1,3-oxazolidin-2-one as intermediate. The synthesis of the indolenines can be carried out in two stages or as a one-pot synthesis without isolation of the oxazolidinones. The solvents used are mineral or silicone oils. The disadvantage of these solvents is the heterogeneous reaction mixture (3 phases: solvent/reaction mixture/catalyst).

It is an object of the present invention to eliminate the aforementioned disadvantages.

We have found that this object is achieved by a novel and improved process for preparing indolenines of the general formula I

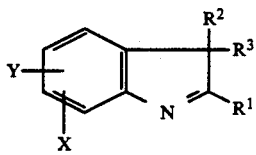

where
R$^1$, R$^2$ and R$^3$ are independently of one another hydrogen, C$_1$–C$_{20}$-alkyl, C$_2$–C$_{20}$-alkenyl, C$_3$–C$_8$-cycloalkyl, alkyl, aryl, C$_7$–C$_{20}$-alkylphenyl, C$_7$–C$_{20}$-phenalkyl, or R$^1$ and R$^2$ or R$^1$ and R$^3$ together are an unsubstituted or C$_1$–C$_{12}$-alkyl-substituted C$_3$–C$_8$-alkylene chain, X and Y are independently of one another hydrogen, C$_1$–C$_8$-alkyl, C$_1$–C$_8$-alkoxy, C$_2$–C$_8$-alkoxyalkyl, C$_2$–C$_8$-alkoxycarbonyl, C$_1$–C$_4$-alkylsulfonyl, halogen, nitro or cyano, by reacting a 4-methylene-1,3-dioxolan-2-one of the formula II

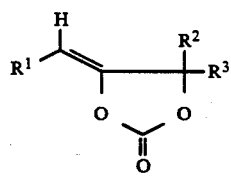

where R$^1$, R$^2$ and R$^3$ are each as defined above, with an aniline of the formula III

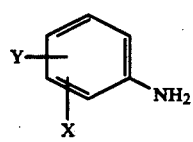

where X and Y are each as defined above, in the presence of a Lewis acid and in the presence or absence of a halide of main group 1 or 2 of the Periodic Table at from 100° to 350° C. and at from 1 to 50 bar, which comprises carrying out the reaction in a polar solvent.

The process according to the present invention can be carried out as follows:

The synthesis of indolenines I by the process according to the present invention can be carried out by introducing the 4-methylene-1,3-dioxolan-2-one II and the aniline III together in a polar solvent with a Lewis acid and with or without a halide of main group 1 or 2 of the Periodic Table and heating the mixture.

It is similarly possible to start only with the aniline III in a polar solvent, a Lewis acid and a halide of group 1 or 2 of the Periodic Table and to add the 4-methylene-1,3-dioxolan-2-one II at the reaction temperature.

It is of course also possible to react the compounds of the formulae II and III, the polar solvent, the Lewis acid and the halide of main group 1 or 2 of the Periodic Table in a continuous process. A continuous process is advantageously carried out using a stirred kettle cascade, in particular a two- or three-kettle cascade.

The reaction of the compound of the formula II with the compound of the formula III takes place with CO$_2$ and H$_2$O elimination.

The process according to the present invention is advantageously carried out at from 100° to 350° C., preferably at from 150° to 300° C., particularly preferably at from 200° to 250° C.

At above 200° C. the reaction is in general carried out at from 1 to 50 bar, preferably at from 1 to 10 bar, particularly preferably at from 2 to 5 bar.

The by-products CO$_2$ and H$_2$O are removed from the system via a pressure control valve.

Suitable polar solvents for the process according to the present invention are high boiling compounds which are inert under the reaction conditions, for example ureas with from one to four C$_1$–C$_8$-alkyl substituents on nitrogen, such as N,N'-dimethyl-, N,N'-diethyl-, N,N'-dipropyl-, N,N'-dibutyl-, N,N,N',N'-tetramethyl- and N,N,N', N'-tetraethyl-urea.

The urea may also for example have a cyclic structure, such as ethyleneurea or propyleneurea and derivatives thereof with one or two C$_1$–C$_8$-alkyl substituents on the nitrogens, such as N,N'-dimethyl- or N,N'-diethyl-ethyleneurea or -propyleneurea.

Solvents suitable for the purposes of the present invention also include cyclic lactams having from 5 to 8 chain members, which may be substituted on the nitrogen by C$_1$–C$_{12}$-alkyl. Examples are pyrrolidone, piperidone and ε-caprolactam and also the N-methyl, N-ethyl, N-propyl, N-butyl, N-hexyl or N-octyl derivatives thereof, in particular N-methylpyrrolidine.

Solvents for the purposes of the present invention further include aliphatic polyalcohols having from 2 to 5 hydroxyl groups, e.g. ethylene glycol, propylene glycol, glycerol, neopentylglycol or pentaerythritol, and also polyethylene glycols, such as diethylene glycol, triethylene glycol, tetraethylene glycol or longer polyethylene glycols having average molecular weights of from 250 to 9000, including in particular those with mono- or di- C$_1$–C$_5$-alkylation at the terminal OH groups, e.g. diethylene glycol monomethyl ether, dimethyl ether, monoethyl ether, diethyl ether, monobutyl ether, dibutyl ether, triethylene glycol monomethyl ether, dimethyl ether, monoethyl ether, diethyl ether, monobutyl ether, dibutyl ether, tetraethylene glycol monomethyl ether, dimethyl ether, monoethyl ether, diethyl ether, monobutyl ether, dibutyl ether or polyethylene glycols of an average molecular weight of from 250 to 9000 as mono- or di- methyl, ethyl or butyl ethers.

Suitable Lewis acids for the reaction are for example aluminum(III), boron(III), iron(III), titanium(IV), zinc(II), tin(II) or tin(IV) salts, preferably the halides thereof, such as chlorides, bromides and iodides, in particular zinc(II) chloride.

Suitable halides of main groups 1 and 2 of the Periodic Table are for example LiCl, NaCl, KCl, LiBr, NaBr, KBr, LiI, NaI, KI, $MgCl_2$, $CaCl_2$, $BaCl_2$, $MgBr_2$, $CaBr_2$, $BaBr_2$, $MgI_2$, $CaI_2$ and $BaI_2$.

The substituents $R^1$, $R^2$, $R^3$, and Y in the compounds I, II and III have the following meanings:

$R^1$, $R^2$ and $R^3$ are each independently of one another hydrogen branched or unbranched $C_1$–$C_{20}$-alkyl, preferably branched or unbranched $C_1$–$C_8$-alkyl, such as n-pentyl, isopentyl, secpentyl, tert-pentyl, neopentyl, 1,2-dimethylpropyl, n-hexyl, isohexyl, sechexyl, n-heptyl, isoheptyl, n-octyl and isooctyl, particularly preferably $C_1$–$C_4$-alkyl such as methyl, ethyl, n-propyl, isopropyl, n-butyl, isobutyl, sec-butyl, tert-butyl, branched or unbranched $C_2$–$C_{20}$-alkenyl, preferably branched or unbranched $C_2$–$C_8$-alkenyl, such as allyl, 2-buten-1-yl, 4-buten-2-yl, 4-buten-1-yl, 2-penten-1-yl and 2,2-dimethylpenten-1-yl, $C_3$–$C_8$-cycloalkyl, such as cyclopropyl, cyclobutyl, cyclopentyl, cyclohexyl, cycloheptyl and cyclooctyl, aryl, such as phenyl, 1-naphthyl and 2-naphthyl, preferably phenyl, $C_7$–$C_{20}$-phenalkyl, preferably $C_a$–$_{C10}$-phenalkyl such as benzyl, 1-phenethyl and 2-phenethyl, $C_7$–$C_{20}$-alkylphenyl, such as 2-methylphenyl, 4-methylphenyl, 2-ethylphenyl, 4-ethylphenyl, 3-methylphenyl, 2,4-dimethylphenyl, 3,4-dimethylphenyl and 3,4,5-trimethylphenyl, $R^1$ and $R^2$ or $R^1$ and $R^3$ together are a $C_2$–$C_8$-alkylene chain, such as $(CH_2)_2$, $(CH_2)_3$, $(CH_2)_4$, $(CH_2)_5$, $(CH_2)_6$, $(CH_2)_7$ and $(CH_2)_8$, preferably $(CH_2)_4$, $(CH_2)_5$ $C_1$–$C_{12}$-alkyl-monosubstituted to -pentasubstituted $C_2$–$C_8$-alkylene, such as $CH_2(CH_3)CH$, $(CH_2)_2CH(CH_3)CH_3$, X and Y are each independently of one another hydrogen branched or unbranched $C_1$–$C_8$-alkyl, such as n-pentyl, isopentyl, sec-pentyl, tert-pentyl, neopentyl, 1,2-dimethylpropyl, n-hexyl, isohexyl, sec-hexyl, n-heptyl, isoheptyl, n-octyl and isooctyl, preferably $C_1$–$C_4$-alkyl such as methyl, ethyl, n-propyl, isopropyl, n-butyl, isobutyl, sec-butyl and tert-butyl, $C_1$–$C_8$-alkoxy, preferably $C_1$–$C_4$-alkoxy, such as methoxy, ethoxy, n-propoxy, isopropoxy, n-butoxy, isobutoxy, sec-butoxy and tert-butoxy, $C_2$–$C_8$-alkoxyalkyl, preferably $C_2$–$C_4$-alkoxyalkyl, such as methoxymethyl, ethoxymethyl, $C_2$–$C_8$-alkoxycarbonyl, preferably $C_2$–$C_4$-alkoxycarbonyl, such as methoxycarbonyl, ethoxycarbonyl, $C_1$–$C_4$-alkylsulfonyl, such as methylsulfonyl, ethylsulfonyl, halogen, such as fluorine, chlorine, bromine and iodine, preferably chlorine and bromine, nitro, cyano.

Preferred indolenines I are for example 2,3,3-trimethyl-3(H)-indole, 2,3,3,5-tetramethyl-3(H)-indole and 5-chloro-2,3,3-trimethyl-3(H)-indole.

The indolenines I preparable by the process according to the present invention are intermediates for preparing cationic cyanine and azacyanine dyes (ref. Ullmann Volume A16, 5th Edition, 487 ff) and also for the photographic industry (e.g. U.S. Pat. No. 3,865,837, Eastman Kodak; EP 288,083 Fuji Photo Film K. K.).

EXAMPLE 1

256 g of 4,4-dimethyl-5-methylene-1,3-dioxolan-2-one, 465 g of aniline, 20 g of $ZnCl_2$, 12 g of LiCl and 70 g of N-methylpyrrolidone are mixed together and stirred at 200° C. for 8 hours. In parallel with the evolution of $CO_2$, $H_2O$ is eliminated and distilled continuously out of the reaction mixture. After the reaction has ended, the subsequent distillation gives 249 g (78%) of 2,3,3-trimethyl-3(H)-indole, boiling point 110° C./10 mmHg.

EXAMPLE 2

465 g of aniline, 20 g of $ZnCl_2$, 12 g of LiCl and 70 g of N-methylpyrrolidone are heated to the refluxing temperature and then admixed with 256 g of 4,4-dimethyl-5-methylene-1,3-dioxolan-2-one in the course of 7 hours. After the dropwise addition has ended, the mixture is stirred at 200° C. for 8 hours and then distilled. This gives 251 g (79%) of 2,3,3-trimethyl-3(H)-indole, boiling point 110° C./10 mmHg.

EXAMPLES 3 TO 17

They are carried out similarly to Example 1 or 2 using 70 g of the solvents listed hereinafter as replacement for N-methylpyrrolidone.

| Solvent | Analogously to Example No. | Yield [%] |
| --- | --- | --- |
| Glycerol | 1 | 63 |
| Glycerol | 2 | 78 |
| Triethylene glycol | 1 | 73 |
| Triethylene glycol | 2 | 73 |
| Neopentylglycol | 2 | 74 |
| Pentaerythritol | 1 | 74 |
| Polyethylene glycol 600 | 2 | 67 |
| Polyethylene glycol 9000 | 2 | 69 |
| Diethylene glycol dibutyl ether | 1 | 79 |
| Polyethylene glycol dimethyl ether 250 | 1 | 80 |
| Polyethylene glycol dimethyl ether 500 | 1 | 79 |
| Polyethylene glycol dimethyl ether 1000 | 2 | 74 |
| N,N-Dimethylurea | 2 | 73 |
| N,N-Dimethylethylurea | 1 | 76 |
| N,N-Dimethylpropyleneurea | 2 | 78 |

EXAMPLES 18 TO 29

They are carried out similarly to Example 1 or 2 using a different Lewis acid and halides of main group 1 and 2 of the Periodic Table (in identical mole equivalents).

| Lewis acid | Halide of main group 1 or 2 of the Periodic Table | Analogously to Example No. | Yield [%] |
| --- | --- | --- | --- |
| $FeCl_3$ | LiCl | 1 | 45 |

-continued

| Lewis acid | Halide of main group 1 or 2 of the Periodic Table | Analogously to Example No. | Yield [%] |
|---|---|---|---|
| AlCl$_3$ | LiCl | 1 | 7 |
| TiCl$_4$ | LiCl | 1 | 8 |
| SnCl$_4$ | LiCl | 1 | 29 |
| ZnCl$_2$ | — | 1 | 68 |
| ZnCl$_2$ | NaCl | 1 | 79 |
| ZnCl$_2$ | KCl | 1 | 78 |
| ZnCl$_2$ | CaCl$_2$ | 1 | 78 |
| ZnCl$_2$ | LiBr | 1 | 77 |
| ZnCl$_2$ | LiI | 2 | 67 |
| ZnBr$_2$ | LiBr | 2 | 63 |
| ZnI$_2$ | LiI | 2 | 56 |

EXAMPLES 30 TO 33

They are carried out similarly to Example 1 using different temperatures, pressures and reaction times.

| Temperature [°C.] | Pressure [bar] | Reaction time [h] | Yield [%] |
|---|---|---|---|
| 210 | 1 | 6 | 80 |
| 220 | 2 | 4 | 79 |
| 230 | 3 | 3 | 82 |
| 240 | 4 | 2 | 81 |

EXAMPLE 34

It is carried out similarly to Example 1 using 535 g of p-toluidine. Distillation gave 258 g (75%) of 2,3,3,5-tetramethyl-3(H)-indole, boiling point 125° C./23 mmHg.

We claim:

1. A process for preparing an indolenine of the formula I

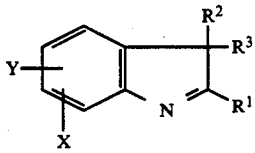

where
R$^1$, R$^2$ and R$^3$ are independently of one another hydrogen, C$_1$–C$_{20}$-alkyl, C$_2$–C$_{20}$-alkenyl, C$_3$–C$_8$-cycloalkyl, phenyl, 1-naphthyl, 2-naphthyl, C$_7$–C$_{20}$-alkylphenyl, C$_7$–C$_{20}$-phenalkyl, or R$^1$ and R$^2$ or R$^1$ and R$^3$ together are an unsubstituted or C$_1$–C$_{12}$-alkyl-substituted C$_3$–C$_8$-alkylene chain, X and Y are independently of one another hydrogen, C$_1$–C$_8$-alkyl, C$_1$–C$_8$-alkoxy, C$_2$–C$_8$-alkoxyalkyl, C$_2$–C$_8$-alkoxycarbonyl, C$_1$–C$_4$-alkylsulfonyl, halogen, nitro or cyano, by reacting a 4-methylene-1,3-dioxolan-2-one of the formula II

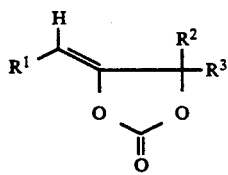

where R$^1$, R$^2$ and R$^3$ are each as defined above, with an aniline of the formula III

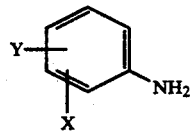

where X and Y are each as defined above, in the presence of a Lewis acid and in the presence or absence of a halide of main group 1 or 2 of the Periodic Table at from 100° to 350° C. and at from 1 to 50 bar, the improvement wherein the reaction is carried out in the presence of a polar solvent.

2. A process as claimed in claim 1, wherein the reaction is carried out at from 200° to 300° C.

3. A process as claimed in claim 1, wherein the reaction is carried out at from 2 to 10 bar.

4. A process as claimed in claim 1, wherein the polar solvent used is a urea with from one to four C$_1$–C$_8$-alkyl substituents on nitrogen, a cyclic urea with one or two C$_1$–C$_8$-alkyl substituents on nitrogen, a cyclic lactam of from 5 to 8 chain members with or without a C$_1$–C$_{12}$-alkyl substituent on the nitrogen, or an aliphatic polyalcohol having from 2 to 5 hydroxyl groups and an average molecular weight of from 200 to 10,000.

5. A process as claimed in claim 1, wherein the polar solvent used is a urea with from one to four C$_1$–C$_8$-alkyl substituents on nitrogen.

6. A process as claimed in claim 1, wherein the polar solvent used is a cyclic urea with one or two C$_1$–C$_8$-alkyl substituents on nitrogen.

7. A process as claimed in claim 1, wherein the polar solvent used is a cyclic lactam of from 5 to 8 chain members with or without a C$_1$–C$_{12}$-alkyl substituent on the nitrogen.

8. A process as claimed in claim 1, wherein the polar solvent used is N-methylpyrrolidone.

9. A process as claimed in claim 1, wherein the polar solvent used is an aliphatic polyalcohol having from 2 to 5 hydroxyl groups and an average molecular weight of from 200 to 10,000.

* * * * *